United States Patent
Gaudin

(10) Patent No.: US 7,683,023 B2
(45) Date of Patent: Mar. 23, 2010

(54) PERFUMING INGREDIENTS OF THE WOODY TYPE

(75) Inventor: Jean-Marc Gaudin, Annemasse (FR)

(73) Assignee: Firmenich SA, Geneva (CH)

( * ) Notice: Subject to any disclaimer, the term of this patent is extended or adjusted under 35 U.S.C. 154(b) by 5 days.

(21) Appl. No.: 11/916,002

(22) PCT Filed: May 26, 2006

(86) PCT No.: PCT/IB2006/051676

§ 371 (c)(1),
(2), (4) Date: Nov. 29, 2007

(87) PCT Pub. No.: WO2007/004080

PCT Pub. Date: Jan. 11, 2007

(65) Prior Publication Data

US 2008/0214432 A1    Sep. 4, 2008

(30) Foreign Application Priority Data

Jul. 1, 2005 (WO) ............... PCT/IB2005/002221

(51) Int. Cl.
*A61K 8/00* (2006.01)
*A61K 8/18* (2006.01)
*C11D 3/50* (2006.01)

(52) U.S. Cl. .......... 512/1; 512/8; 512/22; 512/25; 424/65; 510/106

(58) Field of Classification Search ........... 512/13, 512/22, 1, 25, 8
See application file for complete search history.

(56) References Cited

U.S. PATENT DOCUMENTS

| 4,126,571 | A | * | 11/1978 | Light et al. ........... 510/104 |
| 4,271,046 | A | | 6/1981 | Willis et al. ........... 252/522 R |
| 4,442,025 | A | | 4/1984 | Boelens et al. ........ 252/522 R |
| 4,491,537 | A | | 1/1985 | Fujioka et al. ......... 252/522 R |
| 5,510,326 | A | | 4/1996 | Noire ..................... 512/11 |
| 2005/0004378 | A1 | | 1/2005 | Mane et al. ............ 549/430 |

FOREIGN PATENT DOCUMENTS

| DE | 41 31 119 A1 | 3/1993 |
| FR | 2 831 165 | 4/2003 |
| GB | 1 502 706 | 3/1978 |

OTHER PUBLICATIONS http://www.merriam-webster.com/dictionary/perceive.*
The Random House Dictionary Revised Edition ed. J. Stein, 1980 New York USA p. 985.*
International Search Report and Written Opinion for PCT/IB2006/051676.

* cited by examiner

*Primary Examiner*—James Seidleck
*Assistant Examiner*—Aaron Greso
(74) *Attorney, Agent, or Firm*—Winston & Strawn LLP

(57) ABSTRACT

The present invention relates to the use as perfuming ingredient of a 3,3-dimethylbicyclo[2.2.1]hept-2-yl or a 3,3-dimethylbicyclo[2.2.1]hept-5-en-2-yl derivative, as well as to the compositions or articles containing this compound.

7 Claims, No Drawings

PERFUMING INGREDIENTS OF THE WOODY TYPE

TECHNICAL FIELD

The present invention relates to the field of perfumery. More particularly, it concerns the use as perfuming ingredient of a 3,3-dimethylbicyclo[2.2.1]hept-2-yl or a 3,3-dimethylbicyclo[2.2.1]hept-5-en-2-yl derivative. The present invention concerns the compositions or articles containing said compound.

PRIOR ART

To the best of our knowledge, amongst the compounds of formula (I) only 2-(3,3-dimethylbicyclo[2.2.1]hept-5-en-2-yl)-2-propanol is known. Said compound is mentioned in several documents as chemical intermediate (see for example U.S. Pat. No. 4,491,537).

However, these prior art documents do not report or suggest any organoleptic properties of the compounds of formula (I), or any use of said compound in the field of perfumery. Furthermore, the prior art mentions compositions of the known compounds which are only reactions medium and are by no means perfuming compositions.

DESCRIPTION OF THE INVENTION

We have now surprisingly discovered that a compound of formula

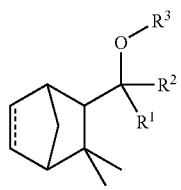

(I)

wherein the dotted line represents a single or double bond;
$R^1$ represents a $C_1$-$C_4$ alkyl or alkenyl group;
$R^2$ represents a methyl or ethyl group; and
$R^3$ represents a hydrogen atom or a methyl, formyl or acetyl group;
in the form of any one of its stereoisomers or of a mixture thereof, can be used as perfuming ingredient, for instance to impart odor notes of the woody type.

The compound of formula (I) can be in the form of any one of its isomers or a mixture thereof, and in particular in the form of an isomer endo or exo, or of a mixture thereof.

According to a particular embodiment of the invention, a compound of formula

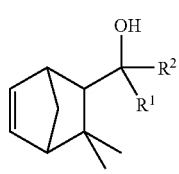

(II)

wherein $R^1$ represents a $C_1$-$C_4$ alkyl or alkenyl group, and $R^2$ represents a methyl or ethyl group; are particularly appreciated.

In particular, 2-(3,3-dimethylbicyclo[2.2.1]hept-5-en-2-yl)-2-propanol, of formula

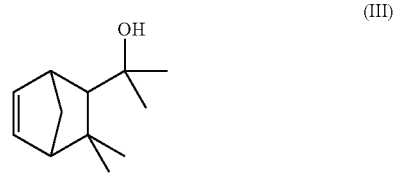

(III)

in the form of any one of its isomers or a mixture thereof; is particularly appreciated by perfumers for its patchouli note. One may also cite a compound of formula (III) in the form of a composition of 2-(3,3-dimethylbicyclo[2.2.1]hept-5-en-2exo-yl)-2-propanol and 2-(3,3-dimethylbicyclo[2.2.1]hept-5-en-2endo-yl)-2-propanol, wherein the endo isomer represents at least 50%, by weight, of the composition.

Amongst the compounds of formula (I), one may cite in particular, and as non-limiting example, 2-(3,3-dimethylbicyclo[2.2.1]hept-5-en-2-yl)-2-propanol, in the form of a mixture of two stereoisomers exo/endo≅30/70. This compound has a woody, patchouli odor with camphor, fruity and tagete notes. The overall odor reminds strongly of the top note of Patchouli essential oil. When compared with the known prior art compound having a patchouli odor, 2-(3,3-dimethylbicyclo[2.2.1]hept-5-en-2-yl)-2-propanol has been perceived by the perfumer as the one having the most natural organoleptic profile.

Other examples of invention's compound are 2-(3,3-dimethylbicyclo[2.2.1]hept-2-yl)-2-propanol or 2-(3,3-dimethylbicyclo[2.2.1]hept-2endo-yl)-2-pentanol which possess an odor of the woody-dry type.

Yet another example of invention's compound is 2-(3,3-dimethylbicyclo[2.2.1]hept-5-en-2-yl)-2-butanol, and in particular its exo isomer, which is characterized by nice pine and borneol notes with a slight camphor bottom note.

Furthermore, 2-(3,3-dimethylbicyclo[2.2.1]hept-5-en-2-yl)-2-hexanol, like its propanol analogue cited above, possesses an odor with woody and patchouli notes, but distinguishes itself from the lower analogue by having also a green note.

Finally, one can cite also 2-(3,3-dimethylbicyclo[2.2.1]hept-5-en-2-yl)-2-penten-2-ol which possesses odor notes of the borneol, green and slightly fatty types.

As mentioned above, the invention concerns the use of a compound of formula (I) as perfuming ingredients. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in perfumery industry as active ingredients.

Said compositions, which in fact can be advantageously employed as perfuming ingredient, are also an object of the present invention.

Therefore, another object of the present invention is a perfuming composition comprising:

i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials, for examples, may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's Verlag-GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient.

Said perfuming co-ingredient is not of the formula (I). Moreover, by "perfuming co-ingredient" it is meant here a compound which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

In particular, it has been found that an invention's composition comprising an invention's compound, in particular 2-(3,3-dimethylbicyclo[2.2.1]hept-5-en-2-yl)-2-propanol, and (5RS,6RS)-2,6,10,10-tetramethyl-1-oxaspiro[4.5]decan-6-ol, for example in the same amount, is particularly appreciated by perfumers due to the presence of a synergistic effect which renders the patchouli note even more natural and long-lasting than for the two separated ingredients.

For the compositions which comprise both a perfumery carrier and a perfumery base, other suitable perfumery carriers than those previously specified can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Its is also understood here that, unless otherwise indicated or described, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:
i) as perfuming ingredient, at least one compound of formula (I), as defined above; and
ii) a consumer product base;

is also an object of the present invention.

For the sake of clarity, it has to be mentioned that, by "consumer product base", we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 30% by weight, or even more, of the compounds of the invention based on the weight of the composition into which they are incorporated. Concentrations lower than these, such as in the order of 0.1% to 15% by weight, can be used when these compounds are incorporated into perfumed articles, percentage being relative to the weight of the article.

The invention's compounds can be synthesized according to the literature, in particular both exo end endo isomers of 2-(3,3-dimethylbicyclo[2.2.1]hept-5-en-2-yl)-2-propanol can be obtained according to Vathke-Ernst H. et al in *Chem. Ber.*, (114), 1981, pg 1464, via addition of the corresponding Grignard reagent to 2-acetyl-3,3-dimethylbicyclo[2.2.1]hept-5-en (see T. Willhalm et al in *Helv. Chim. Acta*, 1967, pg 826).

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacements δ are indicated in ppm with respect to TMS as standard, the coupling constants J are expressed in Hz.

EXAMPLE 1

The preparation of 1-(3,3-Dimethyl-bicyclo[2.2.1]hept-2-yl)-1-ethanone is described in the prior art, as well as its separation in the endo or exo isomers. In the following experimental part said ketone has been used in various exo/endo ratio depending on the desired ratio of the final compound.

Synthesis of Compounds of Formula (I): General Procedure 1-(3,3-Dimethyl-bicyclo[2.2.1]hept-2-yl)-1-ethanone (10 g) was added dropwise at 0° C. for 30 minutes to 1.2 equivalent of methylmagnesium chloride (solution 3 M in THF) or ethylmagnesium chloride (solution 2.8 M in THF) or allylmagnesium chloride (solution 2M in THF). After being stirred for 1 h at 0° C. and overnight at room temperature the solution was cooled to 0° C. and hydrolyzed with a solution of $NH_4Cl$. The aqueous phase was washed three times with ether. The combined ether layer was washed with water, dried over $Na_2SO_4$, and the solvent evaporated. The crude product was then purified by flash chromatography on silica gel (eluent: cyclohexane/AcOEt=2/98).

2-(3,3-dimethylbicyclo[2.2.1]hept-2-yl)-2-propanol—Isolated as a Mixture Exo/Endo=70/30

MS: 182 (1); 167(5); 164(8); 149(30); 124(37); 121(48); 109(28); 93(20); 81(32); 67(31); 59(100) (identical for the both isomers) $^{13}$C-NMR (exo): 41.0 (d); 43.0 (s); 50.4 (d); 65.1 (d); 74.1 (s) $^{13}$C-NMR (endo): 38.0 (s); 41.6 (d); 51.0 (d); 59.0 (d); 74.0 (s)

2-(3,3-dimethylbicyclo[2.2.1]hept-5-en-2-yl)-2-propanol—Isolated as a Mixture Exo/Endo=30/70 endo
$^{13}$C-NMR: 24.9 (q); 30.0 (q); 31.9 (q); 33.8 (q); 42.7 (s); 46.8 (d); 47.7 (t); 56.0 (d); 60.5 (d); 73.2 (s); 133.6 (d); 138.7 (d). $^1$H-NMR: 1.10 (s, 3H); 1.26 (s, 3H); 1.28 (s, 6H); 1.33 (d, J=9 Hz, 1H); 1.40 (s, OH); 1.62 (d, J=9 Hz, 1H); 1.85 (d, J=3 Hz, 1H); 2.29 (m, 1H); 2.93 (m, 1H); 6.23 (dd, $J_1$=7 Hz, $J_2$=3 Hz, 1H); 6.29 (dd, $J_1$=7 Hz, $J_2$=3 Hz, 1H).

exo
$^{13}$C-NMR: 27.0 (q); 29.5 (q); 30.1 (q); 31.6 (q); 40.1 (s); 46.0 (d); 47.0 (t); 55.6 (d); 60.7 (d); 73.6 (s); 135.5 (d); 138.4 (d). $^1$H-NMR: 0.94 (s, 3H); 1.12 (d, J=1 Hz, 1H); 1.27 (d, J=9 Hz, 1H); 1.32 (s, 3H); 1.33 (s, 3H); 1.34 (s, 3H); 1.40 (s, OH); 1.80 (d, J=9 Hz, 1H); 2.26 (m, 1H); 2.69 (m, 1H); 6.09 (dd, $J_1$=7 Hz, $J_2$=3 Hz, 1H); 6.23 (dd, $J_1$=7 Hz, $J_2$=3 Hz, 1H).

2-(3,3-dimethylbicyclo[2.2.1]hept-5-en-2exo-yl)-2-butanol—Isolated as 1 Isomer Exo MS: 194 (1); 176(3); 161(4); 147(4); 133(5); 110(70); 99(100); 95(66); 66(32). $^{13}$C-NMR: 8.3 (q); 24.7 (q); 27.3 (q); 31.5 (q); 35.8 (t); 39.9 (s); 45.2 (d); 47.0 (t); 56.0 (d); 58.6 (d); 75.3 (s); 135.5 (d); 138.6 (d) $^1$H-NMR: 0.90 (t, J=7 Hz, 3H); 0.95 (s, 3H); 1.10 (s, 1H); 1.24 (s, 3H); 1.32 (s, 3H); 1.32 (m, 1H); 1.62 (m, 2H); 1.81 (d, J=7 Hz, 1H); 2.25 (s, 1H); 2.76 (s, 1H); 6.10 (m, 1H); 6.24 (m, 1H).

2-(3,3-dimethylbicyclo[2.2.1]hept-5-en-2-yl)-2-butanol—Isolated as a Mixture of 2 Isomer MS): 194(1); 176(3); 161(4); 147(4); 133(5); 110(70); 99(100); 95(66); 66(32) (identical for both isomer $^{13}$C-NMR (isomer A): 8.0 (q); 75.0 (s); 135.6 (d); 138.3 (d). $^{13}$C-NMR (isomer B): 8.7 (q); 75.6 (s); 135.4 (d); 139.1 (d). $^1$H-NMR (isomer A): 2.24 (s, 1H); 2.90 (s, 1H); 6.09 (m, 1H); 6.30 (m, 1H). $^1$H-NMR (isomer B): 2.28 (s, 1H); 2.60 (s, 1H); 6.22 (m, 2H).

2-(3,3-dimethylbicyclo[2.2.1]hept-5-en-2exo-yl)-4-penten-2-ol—Isolated as 1 Isomer Exo MS: 188(3); 173(4); 145(9); 131(9); 122(33); 107(100); 99(90); 91(37); 66(38). $^{13}$C-NMR: 25.7 (q); 27.3 (q); 31.4 (q); 40.0 (s); 45.3 (d); 46.9 (t); 47.6 (t); 56.0 (d); 59.0 (d); 74.6 (s); 118.8 (t); 134.3 (d); 135.5 (d); 138.5 (d) $^1$H-NMR: 0.94 (s, 3H); 1.10 (s, 1H); 1.28 (s, 3H); 1.35 (m, 1H); 1.35 (s, 3H); 1.50 (OH); 1.82 (d, J=8 Hz, 1H); 2.27 (s, 1H); 2.39 (d, J=8 Hz, 2H); 2.81 (s, 1H); 5.11 (d, J=15 Hz, 1H); 5.15 (d, J=10 Hz, 1H); 5.86 (m, 1H); 6.09 (m, 1H); 6.22 (m, 1H).

EXAMPLE 2

Preparation of a Perfuming Composition

An eau de toilette for man was prepared by admixing the following ingredients:

| Ingredient | Parts by weight |
|---|---|
| Styrallyl acetate | 20 |
| 10%* Aldehyde C 10 | 20 |
| 50%* Aldehyde C 12 | 5 |

-continued

| Ingredient | Parts by weight |
|---|---|
| 10%* Aldehyde MNA | 20 |
| 50%* Undecylenic Aldehyde | 15 |
| Methyl Anthranilate | 10 |
| Astrotone | 200 |
| Bergamote essential oil | 140 |
| 10%* Cannelle Ceylan essential oil | 20 |
| 10%* Cetalox ®¹⁾ | 25 |
| Coumarine | 40 |
| Dihydromyrcenol | 40 |
| 1%* Dorinone ®²⁾ Beta | 20 |
| Estragon | 5 |
| Eugenol F | 10 |
| 10%* Feuilles de Violette Absolute | 5 |
| 10%* Galbanum essential oil | 140 |
| Habanolide ®³⁾ | 50 |
| Iris absolute | 10 |
| Iso E Super ®⁴⁾ | 50 |
| 10%* Isobutylquinoleine | 10 |
| Jasmin absolute | 70 |
| Lilial ®⁵⁾ | 75 |
| Lyral ®⁶⁾ | 150 |
| Alpha iso methyl ionone | 100 |
| 50%* Mousse Chêne essential oil | 110 |
| Muscone | 5 |
| Oliban essential oil | 20 |
| Paradisone ®⁷⁾ | 15 |
| Sandela ®⁸⁾ | 70 |
| Terpineol | 75 |
| Vanilline | 10 |
| Vertofix ®⁹⁾ | 700 |
| Vetyver Haiti essential oil | 100 |
| Wardia ®¹⁰⁾ | 75 |
| Ylang Synth ®¹⁰⁾ | 20 |
| | 2450 |

*in dipropyleneglycol
¹⁾dodecahydro-3a,6,6,9a-tetramethyl-naphtho[2,1-b]furan; origin: Firmenich SA, Geneva, Switzerland
²⁾1-(2,6,6-trimethyl-1-cyclohexen-1-yl)-2-buten-1-one; origin: Firmenich SA, Geneva, Switzerland
³⁾pentadecenolide; origin: Firmenich SA, Geneva, Switzerland
⁴⁾1-(octahydro-2,3,8,8-tetramethyl-2-naphtalenyl)-1-ethanone; origin: International Flavors & Fragrances, USA
⁵⁾3-(4-tert-butylphenyl)-2-methylpropanal; origin: Givaudan-Roure SA, Vernier, Switzerland
⁶⁾4/3-(4-hydroxy-4-methylpentyl)-3-cyclohexene-1-carbaldehyde; origin: International Flavors & Fragrances, USA
⁷⁾(+)-methyl (1R)-cis-3-oxo-2-pentyl-1-cyclopentaneacetate origin: Firmenich SA, Geneva, Switzerland
⁸⁾mixture of 2/3/4-(5,5,6-trimethylbicyclo[2.2.1]hept-2-yl)-1-cyclohexanol and 2-(1,7,7-trimethylbicyclo[2.2.1]hept-2-yl)-1-cyclohexanol; origin: Givaudan-Roure SA, Vernier, Switzerland
⁹⁾methyl cedryl ketone; origin: International Flavors & Fragrances, USA
¹⁰⁾compounded perfumery base; origin: Firmenich SA, Geneva, Switzerland The addition of 50 parts by weight of 2-(3,3-dimethylbicyclo[2.2.1]hept-5-en-2-yl)-2-propanol to the above-described eau de toilette imparted to the latter a clear rooty-woody connotation, of the patchouli type, as well as an improved diffusion and warmness.

EXAMPLE 3

Preparation of a Perfuming Composition
A perfuming composition of the patchouli type was prepared by admixing the following ingredients:

| Ingredient | Parts by weight |
|---|---|
| Methyl dihydroabietate | 430 |
| 10%* Absinthe | 30 |

-continued

| Ingredient | Parts by weight |
|---|---|
| 10%* Cinnamic aldehyde | 15 |
| Borneol | 30 |
| 1%* Chamomile essential oil | 60 |
| Camphre | 50 |
| 10%* Carrot | 30 |
| 10%* Cashmeran ®¹⁾ | 25 |
| Cedar essential oil | 150 |
| Natural civettine | 20 |
| Cypress essential oil | 5 |
| Cypriol | 40 |
| 1%* Ethylpraline | 10 |
| 10%* 2,6,10-Trimethyl-9-undecenal | 10 |
| Gaiac wood essential oil | 60 |
| Galbanum essential oil | 10 |
| 10% * Perhydro-4α,8aβ-dimethyl-4a-naphthalenol | 10 |
| Gurjun Baume | 200 |
| 10%* Ionone Beta | 35 |
| Labdanum essential oil | 10 |
| Methylisoeugenol | 5 |
| 10%* Ethyl heptanoate | 30 |
| 4-Tert-butyl-1-cyclohexanol | 180 |
| 10%* Vanillin | 5 |
| Vetyver Java | 50 |
| | 1500 |

*in dipropyleneglycol
¹⁾1,2,3,5,6,7-hexahydro-1,1,2,3,3-pentamethyl-4-indenone; origin: International Flavors & Fragrances, USA The addition of 500 parts by weight of 2-(3,3-dimethylbicyclo[2.2.1]hept-5-en-2-yl)-2-propanol to the above-described perfuming composition imparted to the latter an evident and very natural woody-rooty (patchouli oil) connotation.

The addition to the above-described perfuming composition of the same amount of 4-tert-butyl-1-cyclohexanol (a compound known in the prior art to impart woody-rooty notes) gave a fragrance less natural and too camphor-like.

The addition of (5RS,6RS)-2,6,10,10-tetramethyl-1-oxaspiro[4.5]decan-6-ol (another compound known in the prior art to impart woody-rooty notes) resulted also in a less natural patchouli note (nor enough rooty). However, the addition to the above-mentioned perfuming composition of 250 parts by weight of 2-(3,3-dimethylbicyclo[2.2.1]hept-5-en-2-yl)-2-propanol and 250 parts by weight of (5RS,6RS)-2,6,10,10-tetramethyl-1-oxaspiro[4.5]decan-6-ol resulted in an unexpected synergetic effect which provided a remarkably natural and balanced patchouli note.

The invention claimed is:
1. A method to confer, enhance, improve or modify the odor properties of a perfuming composition or of a perfumed article, which method comprises adding to said composition or article an effective amount of at least a compound of formula:

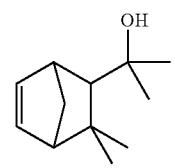

(III)

in the form of any one of its stereoisomers or a mixture thereof.

2. The method of claim 1, wherein the compound is in the form of a mixture of 2-(3,3-dimethylbicyclo[2.2.1]hept-5-en-2exo-yl)-2-propanol and 2-(3,3-dimethylbicyclo [2.2.1]hept-5-en-2endo-yl)-2-propanol, wherein the endo isomer represents at least 50%, by weight, of the composition.

3. The method of claim 1 wherein the compound provides a woody, patchouli odor with camphor, fruity and tagete notes and has a more natural organoleptic profile compared to 2-(3,3-dimethylbicyclo[2.2.1]hept-5-en-2-yl)-2-propanol.

4. A perfuming composition comprising:
   i) a perfuming ingredient of formula

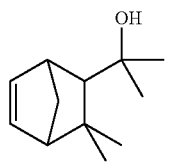

(III)

in the form of anyone of its stereoisomers or of a mixture thereof; and
   ii) at least one ingredient selected from the group consisting of a perfumery carrier and a perfumery base;
   wherein the composition optionally contains at least one perfumery adjuvant.

5. The perfuming composition of claim 4, comprising 2-(3,3-dimethylbicyclo[2.2.1]hept-5-en-2-yl)-2-propanol or (5RS,6RS)-2,6,10,10-tetramethyl-1-oxaspiro[4.5]decan-6-ol, or both.

6. A perfumed article comprising:
   i) a perfuming ingredient of formula

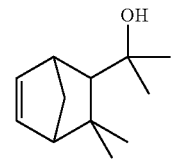

(III)

in the form of anyone of its stereoisomers or of a mixture thereof; and
   ii) a consumer product base.

7. The perfumed article according to claim 6, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

* * * * *